United States Patent [19]

Schoenthal et al.

[11] Patent Number: 4,565,803
[45] Date of Patent: Jan. 21, 1986

[54] METHANOL SYNTHESIS CATALYST

[75] Inventors: Galeon W. Schoenthal, Houston; Lynn H. Slaugh, Cypress, both of Tex.

[73] Assignee: Shell Oil Company, Houston, Tex.

[21] Appl. No.: 562,304

[22] Filed: Dec. 16, 1983

[51] Int. Cl.$^4$ .......................... B01J 21/04; B01J 23/06; B01J 23/10; B01J 23/72

[52] U.S. Cl. ................................... 502/303; 502/302; 502/304; 502/342; 502/524; 518/713

[58] Field of Search ............... 502/302, 303, 304, 342, 502/524; 518/713

[56] References Cited

U.S. PATENT DOCUMENTS

| | | | |
|---|---|---|---|
| 1,707,331 | 4/1929 | Starch . | |
| 3,758,417 | 9/1973 | Magoon et al. | 252/462 |
| 3,850,850 | 11/1974 | Collins | 252/465 |
| 3,923,694 | 12/1975 | Cornthwaite | 252/463 |
| 3,950,369 | 4/1976 | Gent | 260/449.5 |
| 4,181,630 | 1/1980 | Baglin et al. | 252/476 |
| 4,308,176 | 12/1981 | Kristiansen | 252/463 |
| 4,319,037 | 3/1982 | Yoneoka | 560/223 |

FOREIGN PATENT DOCUMENTS

| | | |
|---|---|---|
| 3005551 | 8/1981 | Fed. Rep. of Germany . |
| 54-26983 | 2/1979 | Japan . |

*Primary Examiner*—W. J. Shine

[57] ABSTRACT

A catalyst composition for the conversion of syngas to methanol which comprises copper, zinc and a modifier selected from the group consisting of yttrium, a lanthanide element, an actinide element and mixtures thereof supported on a zinc-aluminum oxide spinel carrier.

10 Claims, No Drawings

METHANOL SYNTHESIS CATALYST

FIELD OF THE INVENTION

This invention relates to catalysts comprising copper and a metal selected from the group consisting of yttrium, a lanthanide element, and actinide element and mixtures thereof supported on a zinc aluminate support which are used for converting carbon monoxide and hydrogen to methanol.

BACKGROUND OF THE INVENTION

U.S. Pat. No. 1,707,331, issued Apr. 2, 1929, discloses the use as methanol synthesis catalysts of copper in combination with fluorides of the cerium family. There is no mention of a zinc aluminate support.

U.S. Pat. No. 3,758,417, issued Sept. 11, 1973, to Magoon et al, discloses a copper, zinc, didymium oxide-containing catalyst which is particularly useful for converting carbon oxides and hydrogen to methanol. This catalyst is prepared by co-precipitation of nitrates at a temperature of about 85° C.–90° C. This reference does not disclose the use of a zinc aluminate support.

U.S. Pat. No. 3,950,369, issued Apr. 13, 1976, discloses a methanol catalyst comprising copper, zinc and a Group II to IV element. The disclosure herein is a generic disclosure with no special preparative techniques indicated.

U.S. Pat. No. 3,923,694 issued Dec. 2, 1975, teaches the use of a zinc aluminate spinel substrate with copper or copper/zinc supported thereon.

U.S. Pat. No. 4,181,630, issued Jan. 1, 1980, discloses a methanol synthesis catalyst comprising copper in combination with an oxide of a rare earth, an actinide element, titanium, zirconium or hafnium. No special preparative techniques are indicated herein. Generally the catalysts are made by first preparing a metal alloy and then oxidizing the alloy to appropriate oxide.

U.S. Pat. No. 4,308,176, issued Dec. 29, 1981, discloses a methanol synthesis catalyst comprising copper mixed with an oxide matrix. In this reference a copper-aluminum oxide spinel is first formed and zinc oxide is subsequently added. Particular care is taken to avoid formation of zinc aluminate spinel.

U.S. Pat. No. 4,319,037, issued Mar. 9, 1982, discloses a catalyst for converting methanol to methyl formate. This catalyst comprises copper plus a Group IIIB or Group IVB or rare earth or actinide element. No particular critical preparative techniques are disclosed, nor is a zinc aluminate spinel support mentioned.

Japanese Patent No. 54 [1979]-26983 published Feb. 28, 1979, discloses as a methanol catalyst a copper, zinc, lanthanum catalyst. This catalyst is prepared by precipitation with alkali metal carbonates. No suggestion of a zinc aluminate spinel support is mentioned.

German Patent No. 3,005,551, published Feb. 14, 1980, discloses a methanol synthesis catalyst comprising copper, zinc and a promoter selected from chromium, cerium, lanthanum, manganese and/or thorium. It is stated that these compounds may be added at any stage in the preparation of the catalyst. It is further stated that addition of compounds such as aluminum oxide lowers catalytic activity.

In application Ser. No. 487,081 filed Apr. 27, 1983 now abandoned, there is disclosed a process for preparing methanol catalysts using alkali metal carbonates as precipitating agents to precipitate copper, zinc and modifier salts at controlled pH levels ranging between about 5.5 and 7.5.

In application Ser. No. 503,984, filed June 13, 1983, now abandoned, there is disclosed a process for preparing methanol catalysts using ammonium carbonate as a precipitating agent to precipitate copper, zinc and modifies salts at controlled pH levels ranging between about 5.5 and 7.5.

SUMMARY OF THE INVENTION

The instant invention relates to a catalyst composition to be used for the conversion of syngas to methanol which composition comprises copper, zinc and a promoter (or modifier) selected from the group consisting of yttrium, a lanthanide element, an actinide element and mixtures thereof supported on a zinc oxide-aluminum oxide spinel support. The catalyst composition is prepared according to this invention by a process which comprises co-precipitating from aqueous solution compounds of zinc and aluminum, then co-precipitating from aqueous solution copper, zinc and promoter compounds in the presence of the first-formed precipitate, washing, drying and calcining the whole precipitate and subsequently activating in a reducing atmosphere.

Catalyst compositions prepared by the instant process provide for catalysts whose activity for the production of methanol from syngas is substantially enhanced over catalysts prepared by traditional methods, such as those taught by U.S. Pat. No. 3,923,694.

DESCRIPTION OF THE PREFERRED EMBODIMENTS

The catalyst compositions prepared herein comprise a mixture of copper, zinc and a promoter metal selected from the group consisting of yttrium, a lanthanide element, an actinide element and mixtures thereof supported on a zinc-aluminum spinel support.

The promoter metals utilized in the instant compositions are selected from yttrium, the Lanthanide series and/or the Actinide series. The Lanthanide series comprises those elements with atomic numbers ranging from 57 (lanthanum) through 71 (lutetium). The Actinide series comprises those elements ranging from atomic number 89 up through atomic number of greater than a 100. The higher numbers, because of scarcity, radio-activity and short lifetimes, do not really make satisfactory catalyst modifiers. Of interest in the Actinide series are those elements ranging from atomic number 89 up to 92 particularly those ranging from 90 to 92, particularly thorium and uranium and most preferably thorium. Mixtures of promoter elements may be suitably utilized. Particularly with regard to the Lanthanide (rare earth) series, mixed metals are readily available commercially. A suitable example of a mixed metal available commercially is the so called "didymium" metal. The composition of didymium is described in U.S. Pat. No. 3,758,417, issued Sept. 11, 1973, incorporated by reference herein. Another commercially available preparation of rare earths is that known as "mischmetal". Other mixtures of rare earths are also available. The preferred modifiers are selected from the group consisting of praseodymium, neodymium, samarium, cerium, yttrium, lanthanum, thorium or mixture thereof.

The precise amount of modifier is not critical. In general, amounts of catalyst modifier of from about 1% to about 25% by weight, based on total catalyst composition and calculated as metal, are satisfactory, with amount of catalyst modifier of from about 4% to about 15% by weight, on the same basis, being preferred.

The relative proportions of copper oxide to zinc oxide to be supported on the spinel support can be varied. In general, ratios from about 1:10 to about 20:1, calculated as weight percent metal, are satisfactory with ratios of from about 1:1 to 10:1, calculated on the same basis, being preferred.

The copper content of the catalyst can lie anywhere within a wide range, e.g. 10–80%. However, for an optimal combination of initial catalytic activity and the stability of that activity during use of the catalyst, a copper content of 25–70% is preferred, especially about 60%. When the copper content is in this preferred range, the total zinc content is preferably less, especially 0.3 to 0.6 of the copper. All these percentages and ratios unless otherwise specified are by metal atoms.

The relative proportions of the zinc and aluminum in the spinel support are preferably within about 10% of the ratio required to form the spinel.

The spinel support oxides preferable constitute from 10–60% by weight of the total catalyst.

The process for preparing the catalysts of the invention comprises co-precipitating from aqueous solution thermally decomposable compounds of aluminum and zinc in proportions capable of forming together a mixed oxide having the spinel structure, then precipitating the copper, zinc and promoter compounds in the presence of the first-formed precipitate, washing the whole precipitate and calcining it to give the metal oxides. The catalyst precursor is subjected to a reduction treatment to give the active catalyst, which constitutes a further feature of the invention.

It will be appreciated that the catalyst is usually stored, handled and sold in the form of its precursor, which indeed is referred to in commerce as the "catalyst", although it is not the catalyst in the strict sense of the agent taking part in chemical reactions such as methanol synthesis. Reduction of the precursor to the catalyst is normally carried out by the operator of the chemical process. The precursor may be in shapes, e.g. pellets, as required by the user of the catalyst, or may be in its condition before the shaping operation, e.g. as powder or lightly compressed powder.

The initial form in which the copper, zinc and modifier are employed is the oxide, although compounds which are readily converted to the oxide, e.g., the corresponding metal carbonates, are also suitably initially employed as these are converted to the oxide, e.g., as during pretreatment subsequent to the formation of the initially prepared catalyst composition. Pretreatment of the catalyst in hydrogen and operation of the catalyst in the reaction environment will cause at least a partial reduction of some of the metals, such as copper, to lower oxidation states, and it is intended that catalysts with these reduced states will fall within the scope of this invention.

The composition of the instant invention are prepared in a specific fashion in order to provide enhanced activity. Generally, the process comprises precipitating from an aqueous solution of aluminum and zinc salts a precipitate which is the precursor for the zinc-aluminum spinel; then, in the presence of the first-formed precipitate, a second precipitate comprising copper, zinc and modifier is formed. The resulting precipitate is washed, dried and calcined. The calcined material is subjected to a reducing treatment to provide the active catalyst.

In the method for making the catalyst the reaction conditions for each precipitation should be carefully controlled. For the second precipitation, and preferably also for the first, the temperature is preferably in the range of about 20°–100° C., preferably about 50°–80° C. and the pH during the precipitating process is maintained between about 5.5 to about 7.5, preferably between about 6.0 and 7.0 and more preferably between about 6.3 and 6.7. The precipitating agent will be an alkali metal or an ammonium carbonate solution. The precipitate thus obtained is a mixture of carbonates, basic carbonates, oxides, hydrated oxides and hydroxides. The first precipitate may be washed before carrying out the second precipitation; whether or not this is done, after the second precipitation, the precipitate is washed substantially free of electrolytes, then dried and calcined, preferably in air, at a temperature of from about 200° C. to about 400° C., a temperature of about 250° C. to about 300° C. being preferred. The drying is carried out at a temperature sufficient to remove the water. This step is conveniently combined with the calcination step by a suitable programming of the temperature from room temperature, slowly through the drying temperature, then up to calcination temperature. The calcined material is shaped, for example, by pelleting under pressure using graphite as a lubricant. The oxide mixture is pretreated in a hydrogen-containing atmosphere prior to use as a catalyst to bring it to its most active state. Pretreatment is accomplished by contacting the catalyst with a stream of hydrogen, of hydrogen mixed with an inert gas or diluent at a temperature ranging from about 175° C. to about 400° C. Suitable diluent gases for the activating gas mixture comprise nitrogen, or oxides of carbon.

In the preferred embodiment, an aqueous solution of aluminum and zinc salts is prepared. Utilized in the most preferred mode are sodium aluminate and zinc nitrate. A second solution of alkali metal or preferably ammonium carbonate is prepared. The two solutions are heated to the desired temperature of 20°–80° C. and simultaneously metered into a precipitation container at individual rates such that the desired pH of 5.5–7.5 is maintained in the precipitation container. Additional diluent water may be used either initially in the precipitation container or added concurrently with the salt solution and precipitating solution. The resulting first precipitate is washed and reslurried with water. Appropriate water soluble salts of copper, zinc and promoter are added to the slurried precipitate. A separate solution of alkali metal or preferably ammonium carbonate is prepared. The slurried solution and the precipitation solution are heated to the desired temperature of 20°–80° C. and simultaneously metered into a precipitation container at individual rates such that the desired pH of 5.5–7.5 is maintained in the precipitation container. Additional diluent water may be used either initially in the precipitation container or added concurrently with the two solutions being metered into the container. The resulting precipitate is thoroughly washed, dried, calcined at about 300° C. and activated in hydrogen at temperatures ranging from about 175°–400° C.

An improved process for converting syngas to methanol is obtained by contacting the catalyst of the instant invention with hydrogen and carbon monoxide or mixtures of carbon oxides (syngas). Molar ratios of hydrogen to carbon oxides range from about 0.5:1 to about 20:1, preferably from about 2:1 to about 10:1. Preferably a molar ratio of hydrogen to carbon monoxide of 2:1 or higher is preferred. Carbon dioxide may be present in the reaction mixture in amounts up to about 50% by weight. Reaction temperatures range from about 200° to about 325° C. with pressures ranging from about atmospheric (15 psia) to about 5000 psia. Gaseous hourly space velocities range from about 5 to about 25000 h$^{-1}$.

The catalyst composition may be employed in batchwise operations or in a continuous manner as by passing the reactants through a tubular reactor containing the catalyst and maintained at reaction temperature.

After reaction, the product mixture is separated and the methanol is recovered by conventional methods, e.g., selective condensation, selective adsorption and the like.

The instant invention will be illustrated by the following illustrative embodiments which are provided for illustration only and are not to be construed as limiting the invention.

ILLUSTRATIVE EMBODIMENTS

Catalyst Preparation

The following example illustrates a typical preparation of catalysts according to the instant invention.

EXAMPLE 1

10.2 Grams (0.047 M) of sodium aluminate was stirred with 55 ml water, followed by addition of 33 ml of nitric acid to get a clear solution. To this solution was added 18.3 g (0.061 M) of zinc nitrate dissolved in 18 ml with water. This solution was heated to 85° C. and added dropwise to 100 ml of water at 65° C. which was vigorously stirred. A 1 M ammonium carbonated solution at ambient temperature was concurrently added at a rate to maintain a pH of 6.5. The precipitate was washed with 800 ml of water after filtration and was reslurried with 800 ml of water. To the slurry was added 176 g (0.595 M) of copper nitrate, 48 g (0.161 M) zinc nitrate and 5 g (0.012 M) of lanthanum nitrate in 200 ml of water and then heated to 85° C. The slurry was added dropwise to a vigorously stirred container having 200 ml of water at 65° C. A 1 M ammonium carbonate solution at 50° C. was also added at a rate to maintain a pH of 6.5. After the final addition of the slurry, the temperature was raised to 85° C. and held there for 20 minutes. The precipitate was filtered out, washed with 1 liter of water and refiltered. The washing and filtration was repeated 5 times. The solid was dried overnight at 120° C. followed by calcination at 300° C. for 4 hours. The dried solid was compressed to 20,000 psig, crushed and sieved to retain 20-30 mesh size. Analysis of this material showed a surface area of 108 m$^2$/g; 60.3% copper, 13.8% zinc, 2.9% lanthanum and 2.1% aluminum. The catalyst was activated by heating in hydrogen by heating gradually over 4 hours to 225° C. and then holding at 225° C. for 90 minutes.

EXAMPLE 2

Example 1 was repeated with the following differences:

1. A 1 M solution of sodium carbonate at 85° C. was used to obtain the first precipitate.

Analysis showed a surface area of 101 m$^2$/g, 60.4% copper, 14.8% zinc, 2.8% lanthanum and 1.4% aluminum.

EXAMPLE 3

Example 1 was repeated with the following differences:

1. A 1 M solution of sodium carbonate at 85° C. was used to obtain both precipitates.

Analysis showed a surface area of 97 m$^2$/g; 66.1% copper, 10.4% zinc, 2.2% lanthanum and 1.0% aluminum.

COMPARATIVE EXAMPLE A

This example was prepared according to the teachings of U.S. Pat. No. 3,923,694 and is similar to Example 1 with the following exceptions:

1. No lanthanum salts were used.
2. A 1 M solution of sodium carbonate at 85° C. was used to obtain both precipitates.
3. The final filter cake was dried for 2 hours in a 120° C. circulating oven and then placed in a 300° C. muffle oven for 6 hours to calcine it.

Analysis showed a surface area of 65 m$^2$/g; 60% copper, 13.4% zinc and 2.5% aluminum.

ILLUSTRATIVE UTILIZATION OF CATALYSTS OF THE INVENTION

The catalysts prepared above were tested for their activity for the conversion of syngas to methanol. 1.5 Milliliters of catalyst diluted with 16 milliliters of inert SiC were loaded into a tube reactor. Syngas (65.9% H$_2$; 19.2% CO and 14.9% CO$_2$) was introduced into the reactor at a temperature of about 240° C. at flow rates corresponding to gaseous hourly space velocities of 12,500. Analyses of the liquid product are shown in Table I. As can be seen in Table I, where lanthanum (Example 3) is added to the teachings of U.S. Pat. No. 3,923,694 (Example A), a significant increase in yield of methanol is obtained. The use of ammonium carbonate in both the first and the second precipitation (Example 1) provides a more active catalyst than when ammonium carbonate is used in the second precipitation and sodium carbonate is used in the first precipitation (Example 2), which is yet more active than the catalyst prepared using sodium carbonate in both precipitations (Example 3).

TABLE I

| Catalyst | Yield of Methanol, g/hr/ml of catalyst |
| --- | --- |
| Example 1 | 2.13 |
| Example 2 | 1.95 |
| Example 3 | 1.64 |
| Example A | 1.44 |

We claim:

1. A catalyst composition to be used for the conversion of syngas to methanol which comprises copper, zinc and a modifier selected from the group consisting of yttrium, a lanthanide element, an actinide element and mixtures thereof supported on a zinc-aluminum oxide spinel carrier wherein the amount of said modifier is from 1 to 25 weight percent based on total catalyst composition, calculated as metal, the relative proportions of copper oxide to zinc oxide are from 1:10 to 20:1, calculated as weight percent metal, wherein said composition is prepared by a process comprising:

a. precipitating a first precipitate from an aqueous solution of dissolved zinc and aluminum salts utilizing as a precipitating agent an aqueous solution of alkali metal or ammonium carbonate, b. slurrying the first precipitate in an aqueous solution containing dissolved salts of copper, zinc and promoter, c. precipitating a second precipitate from the slurry-solution of step b utilizing as a precipitating agent an aqueous solution of alkali metal or ammonium carbonate, d. washing, drying and calcining the precipitate of Step c at a temperature ranging from about 200° C. to about 400° C. and e. activating in a hydrogen-containing atmosphere at a temperature ranging from about 175° C. to about 400° C.

2. The composition of claim 1 wherein the oxide spinel carrier is from 10–60% by weight of the total support.

3. The composition of claim 1 wherein the modifier is present in an amount of from about 4 to about 15 percent and copper and zinc are present in a weight ratio of from about 1:1 to about 10:1.

4. The composition of claim 1 wherein the modifier is selected from the group consisting of yttrium, a lanthanide element, thorium and mixtures thereof.

5. The composition of claim 1 wherein the modifier is praseodymium, neodymium, samarium, cerium, yttrium, lanthanum, thorium or mixtures thereof.

6. The composition of claim 1 wherein the modifier is lanthanum.

7. The composition of claim 1 wherein the second precipitation is carried out at a temperature of from about 20° C. to about 100° C., a pH of from about 5.5 to about 7.5 and ammonium carbonate is utilized as the precipitating agent.

8. The compositon of claim 7 wherein the temperature ranges from about 50° C. to about 80° C. and the pH ranges from about 6 to about 7.

9. The composition of claim 1 wherein the first and second precipitations are carried out at a temperature of from about 20° C. to about 100° C., a pH of from about 5.5 to about 7.5 and ammonium carbonate is utilized as the precipitating agent.

10. The composition of claim 9 wherein the temperature ranges from about 50° C. to about 80° C. and the pH ranges from about 6 to about 7.

* * * * *